US008410022B2

(12) United States Patent
Eaton et al.

(10) Patent No.: US 8,410,022 B2
(45) Date of Patent: *Apr. 2, 2013

(54) GLYPHOSATE SALT HERBICIDAL COMPOSITION

(75) Inventors: David R. Eaton, Kirkwood, MO (US); Jeffrey A. Graham, Chesterfield, MO (US); Henry Agbaje, Greensboro, NC (US)

(73) Assignee: Monsanto Technology LLC, St. Louis, MO (US)

( * ) Notice: Subject to any disclaimer, the term of this patent is extended or adjusted under 35 U.S.C. 154(b) by 1434 days.

This patent is subject to a terminal disclaimer.

(21) Appl. No.: 11/204,322

(22) Filed: Aug. 15, 2005

(65) Prior Publication Data

US 2006/0040826 A1    Feb. 23, 2006

Related U.S. Application Data

(60) Provisional application No. 60/603,232, filed on Aug. 19, 2004.

(51) Int. Cl.
*A01N 25/00* (2006.01)
*A01N 31/00* (2006.01)
*A01N 37/00* (2006.01)

(52) U.S. Cl. ............... 504/116.1; 504/320; 504/353

(58) Field of Classification Search .......... 504/206, 504/362, 116.1, 320, 353
See application file for complete search history.

(56) References Cited

U.S. PATENT DOCUMENTS

| | | | |
|---|---|---|---|
| 3,799,758 A | 3/1974 | Franz | |
| 3,853,530 A | 12/1974 | Franz | |
| 4,405,531 A | 9/1983 | Franz | |
| 5,652,197 A | 7/1997 | Claude et al. | 504/206 |
| 5,668,085 A | 9/1997 | Forbes et al. | 504/206 |
| 5,750,468 A | 5/1998 | Wright et al. | 504/206 |
| 5,863,863 A | 1/1999 | Hasebe et al. | |
| 5,994,269 A | 11/1999 | Bugg et al. | |
| 6,121,199 A | 9/2000 | Berger et al. | 504/206 |
| 6,455,473 B2 | 9/2002 | Wright | 504/206 |
| 6,544,930 B2 | 4/2003 | Wright | 504/206 |
| 6,881,707 B2 | 4/2005 | Howat et al. | 504/206 |
| 6,992,045 B2 * | 1/2006 | Xu et al. | 504/206 |
| 2002/0065199 A1 | 5/2002 | Wright | 504/206 |
| 2002/0123430 A1 | 9/2002 | Xu et al. | |
| 2003/0125209 A1 | 7/2003 | Tank | 504/206 |
| 2003/0158042 A1 | 8/2003 | Bramati et al. | |

FOREIGN PATENT DOCUMENTS

| | | |
|---|---|---|
| AU | 2002325065 B2 | 7/2002 |
| AU | 2005277578 B2 | 8/2005 |
| EP | 1781105 B1 | 12/2008 |
| MX | 2007002005 | 5/2007 |
| WO | WO 92/11764 | 7/1992 |
| WO | WO 96/32839 | 10/1996 |
| WO | WO 99/04635 | 2/1999 |
| WO | WO 99/21424 | 5/1999 |
| WO | WO 00/15037 | 3/2000 |
| WO | WO 00/30451 | 6/2000 |
| WO | WO 01/26463 | 4/2001 |
| WO | WO 01/26469 | 4/2001 |
| WO | WO 01/26469 A1 | 4/2001 |
| WO | WO 01/89302 | 11/2001 |
| WO | WO 03/013241 * | 2/2003 |
| WO | WO 2006/023431 A2 | 3/2006 |

OTHER PUBLICATIONS

Opposition of Australian Patent Application 2005277578 (in the name of Monsanto Technology LLC) by Nufarm Australia Limited, and additional related documents filed in connection with Opposition, 344 pages, Apr. 20, 2011.
Franz et al., Glyphosate: A Unique Global Herbicide, ACS Monograph 189: cover page, index page, and Chapter 7 (pp. 187-219) (1997).
Australian Weed Control Handbook, Tenth Edition, Inkata Press, A Division of Butterwoth-Heinemann, Touchdown Herbicide: cover page, index page, and pp. 487-494 (10 total pages) (1995).
Leaflet, Touchdown@Herbicide, Crop Care Australasia Pty Ltd, 11 pages, received Apr. 20, 2011.
Roundup CT Xtra, Broadacre herbicide by Monsanto: pp. 1-12 (7 total pages), Nov. 1999.
Nufarm Credit® Broadhectare Herbicide, 2 pages, Oct. 28, 2002.
Ingredients in "TillMaster" herbicide, 4 pages, Dec. 1992.
Opposition of Australian Patent Application 2005277578 (in the name of Monsanto Technology LLC) by Nufarm Australia Limited—Additional documents filed in connection with Opposition: Request for Withdrawal of Opposition by Nufarm Australia Limited, 2 pages, May 2, 2011.
Opposition of Australian Patent Application 2005277578 (in the name of Monsanto Technology LLC) by Nufarm Australia Limited—Additional documents filed in connection with Opposition: Acknowledgement by IP Australia of Withdrawal of Opposition by Nufarm Australia Limited, 1 page, May 5, 2011.
Franz, J.E., et al., Glyphosate: A unique global herbicide, ACS Monograph 189, American Chemical Society, Washington, DC (1997), 17 pages.

(Continued)

*Primary Examiner* — Mina Haghighatian
*Assistant Examiner* — Helen Chui
(74) *Attorney, Agent, or Firm* — Joseph A. Schaper; Harness, Dickey & Pierce, P.L.C.

(57) ABSTRACT

A herbicidal composition comprises in aqueous solution a mixture of salts of glyphosate at a total glyphosate a.e. concentration not less than about 360 g/l, wherein (a) said glyphosate is in anionic form accompanied by low molecular weight non-amphiphilic cations in a total molar amount of about 100% to about 120% of the molar amount of said glyphosate; (b) said cations comprise potassium and propylammonium (e.g., isopropylammonium) cations in a mole ratio of about 70:30 to about 90:10; and (c) said potassium and propylammonium cations together constitute about 90 to 100 molar percent of all of said low molecular weight non-amphiphilic cations in the composition.

19 Claims, 2 Drawing Sheets

OTHER PUBLICATIONS

Glyphosate entry in The Pesticide Manual, (1994), 6 pages.
J.B. Wyrill and O.C. Burnside, Glyphosate Toxicity to Common Milkweed and Hemp Dogbane as Influenced by Surfactants published in Weed Science, vol. 25 (No. 3) May 1977, 13 pages.
Opposition of Australian Patent Application 2005277578 (in the name of Monsanto Technology LLC) by Nufarm Australia Limited and related documents filed in connection with Opposition, initiated Jun. 18, 2010, 378 pages.
Schönherr, Jörg, A mechanistic analysis of penetration of glyphosate salts across astomatous cuticular membranes, Society of Chemical Industry, 2002, pp. 343-351.
Grossbard, E. and D. Atkinson. The Herbicide Glyphosate. London: Butterworths, 1985, Table of Contents.
PCT International Search Report (Form PCT/ISA/210) for PCT/US2005/028930.

* cited by examiner

GLYPHOSATE SALT HERBICIDAL COMPOSITION

This application claims the benefit of U.S. provisional patent application Ser. No. 60/603,232, filed on Aug. 19, 2004, the entire disclosure of which is incorporated by reference herein.

FIELD OF THE INVENTION

The present invention relates to aqueous concentrate formulations of the herbicide glyphosate, suitable for dilution in water to prepare herbicidal solutions for application to foliage of a plant to kill or control growth of the plant. In particular, the invention relates to such formulations having improved handling properties.

BACKGROUND OF THE INVENTION

Economics of distribution of agricultural chemicals, such as herbicides in general and glyphosate formulations in particular, can be much improved through provision of a high "loading" of active ingredient in the formulation, that is, the amount of active ingredient that can be accommodated in a container of given capacity.

Glyphosate is an acid that is relatively insoluble in water (1.16% by weight at 25° C.). For this reason it is typically formulated as a water-soluble salt in aqueous solution. A useful alternative is to prepare glyphosate as a dry salt in powder or granular form. For example, a dry water-soluble granular formulation of glyphosate ammonium salt can have a glyphosate acid equivalent (a.e.) content as high as about 86% by weight. This would appear at first sight to provide an excellent solution to the challenge of packing more glyphosate into a container of given capacity. Unfortunately the benefit of a dry glyphosate formulation in this regard is more limited than one might expect, because such a formulation tends to have low bulk density. Also, many end-users and many distributors prefer a liquid product because of flexibility in handling, thus a need remains for high-loaded liquid formulations of glyphosate.

U.S. Pat. No. 6,544,930 to Wright discloses an approach to meeting this challenge. According to this approach, a concentrated aqueous solution of glyphosate, predominantly in the form of one or a mixture of the potassium and monoethanolammonium (MEA) salts thereof, was provided, it having been determined that such a solution had an unexpectedly high specific gravity, permitting more glyphosate a.e. to be delivered in a container of given capacity than was previously attainable using the isopropylammonium (IPA) salt in widespread commercial use, for example as Roundup® herbicide of Monsanto.

Unfortunately, glyphosate potassium salt, especially when formulated at high concentration in aqueous solution, brings some challenges of its own. For example, where (as often) it is desired to coformulate a surfactant with the glyphosate, physical incompatibility of the surfactant with the glyphosate salt can limit the options available. Whereas a wide range of surfactant types are compatible with glyphosate IPA salt, only a few types have been found to be compatible with glyphosate potassium salt, in particular where the salt is present at high concentration. See above-cited U.S. Pat. No. 6,544,930, col. 9, lines 6-13.

International Patent Publication No. WO 01/26469 discloses that aqueous formulations of glyphosate, including highly concentrated formulations, can be prepared using a mixture of glyphosate IPA and ammonium salts at a weight ratio (expressed on a glyphosate a.e. basis) of 80:20 to 97:3. Such formulations are said to exhibit reduced viscosity, leading to greater ease of pumping and handling.

International Patent Publication No. WO 03/013241 proposes, inter alia, a glyphosate composition comprising IPA and potassium cations in a mole ratio of 1:10 to 30:1, "more preferably less than 15:1 and greater than 1:2", reportedly as a means to improve bioefficacy over compositions of a single glyphosate salt.

Publications cited above are incorporated herein by reference.

Considering the variety of conditions and special situations under which glyphosate herbicides are used around the world, there remains a need for aqueous concentrate formulations of glyphosate, including surfactant-containing formulations, providing benefits under at least some of those conditions and situations. There is an especial need for such formulations having high glyphosate loading, for example at least about 400 g a.e./l.

SUMMARY OF THE INVENTION

It has now surprisingly been found that addition of a minor amount of glyphosate IPA salt to a glyphosate potassium salt formulation greatly enhances compatibility with surfactants, and still more surprisingly that, with such addition, acceptable surfactant compatibility can be maintained at high glyphosate a.e. loadings. Furthermore, as will become clear from the description that follows, a number of additional unexpected benefits have been realized in at least some cases by such addition.

Accordingly, there is now provided a herbicidal composition comprising in aqueous solution a mixture of salts of glyphosate at a total glyphosate a.e. concentration not less than about 360 g/l, wherein (a) said glyphosate is in anionic form accompanied by low molecular weight non-amphiphilic cations in a total molar amount of about 100% to about 120% of the molar amount of said glyphosate; (b) said cations comprise potassium and propylammonium (e.g., IPA) cations in a mole ratio of about 70:30 to about 90:10; and (c) said potassium and propylammonium cations together constitute about 90 to 100 molar percent of all of said low molecular weight non-amphiphilic cations in the composition.

There is also provided a composition as just described, further comprising at least one surfactant, wherein the weight ratio of glyphosate (expressed as a.e.) to surfactant is not greater than about 10:1.

In an embodiment of the invention, a composition comprising a mixture of propylammonium (e.g., IPA) and potassium salts of glyphosate further comprises as a major or sole surfactant component a surfactant having a polyoxyethylene moiety comprising on average at least about 7 ethylene oxide (EO) units. It is found that such surfactants promote tank-mix compatibility of the composition with suspension concentrate formulations of coherbicides of low water solubility such as atrazine, diuron, fluometuron or prometryn. Accordingly, there is provided a tank-mix herbicidal composition comprising, in an aqueous application medium, a glyphosate herbicide and a coherbicide of low water solubility, the composition being prepared by a process comprising admixing in a suitable vessel with agitation:

(i) water in an amount suitable for application to a plant and/or soil surface by spraying;
(ii) a herbicidally effective amount of an aqueous concentrate herbicidal composition comprising in aqueous solution a mixture of salts of glyphosate at a total glyphosate a.e. concentration not less than about 360 g/l, wherein (a) said glyphosate is in anionic form accompanied by low molecular weight non-amphiphilic cations in a total molar amount of about 100% to about 120% of the molar amount of said glyphosate; (b) said cations comprise potassium and propylammonium cations in a mole ratio of about 50:50 to about 90:10; and (c) said potassium and propylammonium cations together constitute about 90 to 100 molar percent of all of said low molecular weight non-amphiphilic cations in the composition; said composition further comprising as a major or sole surfactant component a polyoxyethylene tertiary amine or etheramine surfactant comprising on average at least about 7 EO units; and (iii) a herbicidally effective amount of a suspension concentrate formulation comprising the coherbicide.

There is still further provided a batchwise process for preparing a glyphosate salt solution that comprises potassium and IPA cations in a mole ratio of about 50:50 to about 90:10 and has a glyphosate a.e. concentration not less than about 360 g/l, the process comprising at least two steps. In a first step, glyphosate acid is added to a glyphosate potassium salt solution having a glyphosate assay of at least about 40% a.e. by weight, to form a slurry. In a second step, isopropylamine, in an amount sufficient to neutralize the added glyphosate acid, is introduced to the slurry with mixing until all glyphosate is dissolved, to form a mixed glyphosate salt solution comprising potassium and IPA cations in the desired mole ratio.

In an optional third step of the process, water is added to the mixed glyphosate salt solution to adjust glyphosate a.e. concentration of the mixed salt solution to a desired level not less than about 360 g/l.

There is still further provided a continuous process for preparing a finished composition in a form of a glyphosate salt solution that comprises potassium and IPA cations in a mole ratio of about 50:50 to about 90:10 and has a glyphosate a.e. concentration not less than about 360 g/l. In a first step of this process, to recycled finished composition in a first vessel is continuously added glyphosate acid, with agitation, to form a slurry. The slurry is continuously transferred to a second vessel, where, in a second step, with continued agitation of the slurry, potassium hydroxide (KOH) and isopropylamine are continuously added in the desired mole ratio and in a total amount sufficient to neutralize the glyphosate acid added in the first step. Water is added if necessary to adjust the resulting solution to the desired glyphosate a.e. concentration, and the resulting finished composition is drawn from the second vessel. The finished composition is continuously divided into a first stream that is recycled to the first vessel and a second stream that is removed as product.

DETAILED DESCRIPTION OF THE INVENTION

In one embodiment, an aqueous concentrate glyphosate herbicidal composition is provided. The composition of this embodiment takes the form of an aqueous solution comprising a mixture of salts of glyphosate at a total glyphosate a.e. concentration not less than about 360 g/l. For example, in certain compositions the total glyphosate a.e. concentration is not less than about 400 g/l. Such compositions thus share advantages of high glyphosate loading previously disclosed for potassium glyphosate compositions in above-cited U.S. Pat. No. 6,544,930.

By "total glyphosate a.e. concentration" is meant the concentration of glyphosate in all forms present, expressed as acid equivalent. An upper limit for such concentration is dictated by the limit of solubility of the particular salt mixture selected, but in absence of other ingredients such as a surfactant a total glyphosate a.e. concentration of up to about 650 g/l or even higher can be achieved in some instances. Thus the total glyphosate a.e. concentration according to the present embodiment can illustratively be about 400 to about 650 g/l, for example about 450 to about 600 g/l or about 500 to about 600 g/l.

The composition of the present embodiment is further characterized as follows.

First, the glyphosate is in anionic form accompanied by low molecular weight non-amphiphilic cations in a total molar amount of about 100% to about 120% of the molar amount of the glyphosate. In other words, the composition has a mole ratio of glyphosate anions to low molecular weight non-amphiphilic cations of about 1:1.0 to about 1:1.2. This in itself is not unusual; commercial formulations based on the IPA salt of glyphosate are commonly no more than about 5% to about 10% over-aminated (i.e., comprise IPA cations in a molar amount of about 105% to about 110% of the molar amount of glyphosate) and the active ingredient of such formulations is often referred to as "mono(isopropylammonium) glyphosate" to reflect a glyphosate/IPA mole ratio close to 1:1. A mole ratio of anions to cations substantially lower than about 1:1.0, at the high concentrations required by the present invention, is strongly disadvantageous due to promotion of glyphosate acid precipitation. Increasing the mole ratio of anions to cations substantially above 1:1.2 not only adds unnecessary cost through the resulting excess of the cationic species used, but can reduce the upper limit of solubility of the salt mixture, especially in presence of surfactant. It is also known that higher glyphosate/cation mole ratios can, at high concentrations, lead to increased viscosity (see, for example, U.S. Patent Application Publication No. 2003/0125209, incorporated herein by reference). Thus, for practice of the present invention, a total molar amount of low molecular weight non-amphiphilic cations of about 100% to about 120% of the molar amount of glyphosate is highly desirable.

The total molar amount of low molecular weight non-amphiphilic cations can illustratively be about 100% to about 115%, or about 105% to about 110%, of the molar amount of the glyphosate.

The term "low molecular weight non-amphiphilic cation" herein distinguishes the cations of present interest from higher molecular weight cationic entities that can be contributed by certain surfactants such as polyoxyethylene tertiary amines, etheramines and quaternary ammonium surfactants. It will be understood, therefore, that such higher molecular weight entities, even if present, are not to be included in any calculation of total molar amount of cations for purposes of the invention. Low molecular weight non-amphiphilic cations illustratively include alkali metal cations such as potassium and sodium cations, ammonium cations, organic ammonium cations such as propylammonium (n-propylammonium and isopropylammonium), mono- and diethanolammonium cations, and organic sulfonium cations such as trimethylsulfonium cations.

Second, the low molecular weight non-amphiphilic cations present in a composition of the present embodiment comprise potassium and propylammonium cations in a mole ratio of about 70:30 to about 90:10.

The propylammonium cations can consist entirely of n-propylammonium cations, entirely of isopropylammonium cations, or of a mixture thereof at any desired ratio.

It will be noticed that the mole ratio of potassium to propylammonium cations according to the present embodiment lies outside the "preferred" range of above-cited WO 03/013241, which recites an IPA/potassium mole ratio "greater than 1:2", equivalent to a potassium/propylammonium mole ratio lower than 67:33.

At a mole ratio of potassium to propylammonium lower than about 70:30, it becomes more difficult to provide a storage stable composition with high glyphosate loading as desired herein. At a mole ratio higher than about 90:10 the advantages of surfactant compatibility are reduced. Thus, for practice of the present invention, a potassium/propylammonium cation mole ratio of about 70:30 to about 90:10 is highly desirable.

The mole ratio of potassium to propylammonium (e.g., IPA) cations can illustratively be about 2.5:1 to about 7.5:1 (i.e., about 71:29 to about 88:12), for example about 3:1 to about 6:1 (i.e., about 75:25 to about 86:14). In various embodiments the mole ratio of potassium to propylammonium (e.g., IPA) cations is about 75:25 to about 85:15, or about 77:23 to about 83:17, illustratively about 80:20.

Third, the potassium and propylammonium cations present in a composition of the present embodiment together constitute about 90 to 100 molar percent of all low molecular weight non-amphiphilic cations in the composition. In other words, other low molecular weight non-amphiphilic cations such as sodium, ammonium or MEA cations can optionally be present, up to a maximum of about 10 molar percent of all low molecular weight non-amphiphilic cations. Presence of larger amounts of such other cations can lead to difficulties in achieving the desired high loading and/or to reduced surfactant compatibility.

Illustratively, low molecular weight non-amphiphilic cations other than potassium and propylammonium constitute no more than about 5 molar percent, for example no more than about 2 molar percent, of all such cations present. A composition of the invention can be substantially free of low molecular weight non-amphiphilic cations other than potassium and propylammonium cations.

While a composition of the invention can consist essentially of nothing more than the above-described mixture of glyphosate salts in aqueous solution, advantages of the invention become particularly great when one or more surfactants are also included in the composition in an agronomically useful amount.

An "agronomically useful amount" means a sufficient amount of the surfactant or surfactants to provide a benefit in terms of improved herbicidal effectiveness by comparison with an otherwise similar glyphosate composition lacking surfactant. What constitutes an agronomically useful amount depends on the particular surfactant(s) selected, the plant species to be treated with the herbicidal composition, application spray volume, environmental and other factors. Typically a minimum agronomically useful amount is about 1 part by weight of total surfactant per 10 parts by weight of glyphosate acid equivalent.

Thus, in one embodiment, a herbicidal composition is provided as described hereinabove, further comprising at least one surfactant, wherein the weight ratio of glyphosate a.e. to total surfactant is not greater than about 10:1, for example about 2:1 to about 10:1. Illustratively the weight ratio of glyphosate a.e. to total surfactant is about 2.5:1 to about 8:1, for example about 3:1 to about 6:1.

The choice of surfactant or surfactants is not narrowly critical. One of ordinary skill in the art will be able to select a suitable surfactant or surfactant blend from among those known to enhance herbicidal effectiveness of glyphosate by routine experimentation based upon the information provided herein and in the literature pertaining to glyphosate formulations. See, for example, surfactants disclosed as components of glyphosate formulations in the patents and publications individually cited below, each incorporated herein by reference.

U.S. Pat. No. 6,455,473 to Wright.
International Patent Publication No. WO 99/21424.
International Patent Publication No. WO 01/89302.
Above-cited WO 03/013241.

The surfactant(s) can be present in solution (e.g., micellar solution) and/or in stable dispersion, for example as a suspension, emulsion or microemulsion, in the composition.

A surfactant that is a "major or sole surfactant component" herein constitutes about 50% to 100% by weight of all surfactants present in the composition. For the present purpose, the weight or concentration of a surfactant component as defined herein does not include non-amphiphilic compounds that are sometimes introduced with the surfactant component, such as water, isopropanol or other solvents, or glycols, such as ethylene glycol, propylene glycol or polyethylene glycols.

In one embodiment the composition comprises one or more surfactants each having a molecular structure comprising:

(a) a hydrophobic moiety having one to a plurality of aliphatic, alicyclic or aromatic $C_{3-18}$ hydrocarbyl or hydrocarbylidene groups joined together by 0 to about 7 linkages selected from ether, thioether, sulfoxide, ester, thioester and amide linkages, the hydrophobic moiety having in total about 8 to about 24 carbon atoms; and (b) a hydrophilic moiety that comprises:
   (i) an amino group that is cationic or that can be protonated to become cationic, having attached directly thereto 0 to 3 oxyethylene groups or polyoxyethylene chains, such oxyethylene groups and polyoxyethylene chains comprising on average no more than about 15 oxyethylene units per surfactant molecule; and/or
   (ii) a glycoside or polyglycoside group comprising on average no more than about 2 glycoside units per surfactant molecule;

the hydrophobic moiety being covalently attached (1) directly to an amino group of the hydrophilic moiety; (2) by an ether linkage incorporating an oxygen atom of an oxyethylene group or of a terminal oxyethylene unit of a polyoxyethylene chain of the hydrophilic moiety; or (3) by an ether linkage to a glycoside unit of the hydrophilic moiety.

According to the present embodiment, two subclasses of surfactant, defined by formulas (I) and (II) below, can be particularly useful.

A major or sole surfactant component can comprise one or more compounds having, at a pH of about 4, formula (I):

where $R^1$ is hydrogen or $C_{1-18}$ hydrocarbyl, each X is independently an ether, thioether, sulfoxide, ester, thioester or amide linkage, each $R^2$ is independently $C_{3-6}$ hydrocarbylidene, m is an average number of 0 to about 8 such that the total number of carbon atoms in $R^1$—$(XR^2)_m$ is about 8 to about 24, n is an average number of 0 to about 5, $R^3$ and $R^4$ are independently hydrogen or $C_{1-4}$ alkyl, p is 2 to 4, q is 0 or 1, glu is a unit of formula (referred to herein as a glucoside unit), r is an average number of about 1 to about 2, A is an anionic entity, and s is an integer of 1 to 3 and t is 0 or 1 such that electrical neutrality is maintained.

A major or sole surfactant component can comprise one or more compounds having, at a pH of about 4, formula (II):

where $R^1$, X, $R^2$, m, n, A, s and t are as defined above for formula (I), $R^5$ is hydrogen, $C_{1-4}$ alkyl, benzyl, an anionic oxide group or an anionic group $-(CH_2)_uC(O)O$ where u is 1 to 3, $R^6$ and $R^7$ are independently hydrogen, $C_{1-4}$ alkyl, $C_{2-4}$ acyl or $C_{1-4}$ carboxylic acid groups or $C_{1-4}$ alkyl esters of $C_{1-4}$ carboxylic acid groups, and x and y are average numbers such that x+y+n is not greater than about 15.

Surfactants conforming to formulas (I) and (II) above include without restriction those that are or can be described as alkyl polyglucosides, alkylaminoglucosides, polyoxyethylene alkylamines, polyoxyethylene alkyletheramines, alkyltrimethylammonium salts, alkyldimethylbenzylammonium salts, polyoxyethylene N-methyl alkylammonium salts, polyoxyethylene N-methyl alkyletherammonium salts, alkyldimethylamine oxides, polyoxyethylene alkylamine oxides, polyoxyethylene alkyletheramine oxides, alkylbetaines, alkylamidopropylamines and the like. The word or part-word "alkyl" as used in this paragraph reflects common usage in the art and means $C_{8-18}$ aliphatic, saturated or unsaturated, linear or branched hydrocarbyl.

When a maximum or minimum "average number" is recited herein with reference to a structural feature of a surfactant such as oxyethylene or glucoside units, it is to be understood that the integer number of such units in individual molecules in a surfactant preparation typically varies over a range that can include integer numbers greater than the maximum "average number" or smaller than a nonzero minimum "average number". The presence in a composition of individual surfactant molecules having an integer number of such units outside the stated range of "average number" does not remove the composition from the scope of the present embodiments, so long as the "average number" is within the stated range and other requirements are met.

Illustrative surfactant types that can be useful in compositions of the invention include those classified as types A to F below.

Type A: surfactants corresponding to formula (I) where $R^1$ is a $C_{8-18}$ aliphatic hydrocarbyl chain, m, n and q are 0, s is 1 and t is 0. This type includes several commercial surfactants collectively known in the art or referred to herein as alkyl polyglucosides or APGs. Suitable examples are sold by Cognis as Agrimul™ PG-2069 and Agrimul™ PG-2067.

Type B: surfactants corresponding to formula (II) where $R^1$ is a $C_{8-18}$ aliphatic hydrocarbyl chain and m is 0. In this type $R^1$ alone can be considered the hydrophobic moiety of the surfactant and is attached directly to the amino function, as in alkylamines, or by an ether linkage formed by the oxygen atom of an oxyethylene group or the terminal oxygen atom of a polyoxyethylene chain, as in certain alkyletheramines. Illustrative subtypes having different hydrophilic moieties include those classified as subtypes B1 to B5 below.

Subtype B1: x and y are 0, $R^5$ and $R^6$ are independently $C_{1-4}$ alkyl, $R^7$ is hydrogen and t is 1. This subtype includes (where $R^5$ and $R^6$ are methyl) several commercial surfactants collectively known in the art or referred to herein as alkyldimethylamines. Suitable examples are dodecyldimethylamine, available for example from Akzo-Nobel as Armeen™ DM12D, and cocodimethylamine and tallowdimethylamine, available for example from Ceca as Noram™ DMC D and Noram™ DMS D respectively. Such surfactants are generally provided in non-protonated form, the anion A not being supplied with the surfactant. However, in a glyphosate salt formulation at a pH of about 4-5, the surfactant will be protonated and it will be recognized that the anion A can be glyphosate, which is capable of forming dibasic salts.

Subtype B2: x and y are 0, $R^5$, $R^6$ and $R^7$ are independently $C_{1-4}$ alkyl and t is 1. This subtype includes (where $R^5$, $R^6$ and $R^7$ are methyl and A is a chloride ion) several commercial surfactants collectively known in the art or referred to herein as alkyltrimethylammonium chlorides. A suitable example is cocoalkyl trimethylammonium chloride, available for example from Akzo-Nobel as Arquad™ C.

Subtype B3: x and y are average numbers such that x+y is at least 2, $R^6$ and $R^7$ are hydrogen and t is 1. This subtype includes commercial surfactants collectively known in the art or referred to herein as polyoxyethylene alkylamines (where n is 0 and $R^5$ is hydrogen), certain polyoxyethylene alkyletheramines (where n is 1-5 and $R^5$ is hydrogen), polyoxyethylene N-methyl alkylammonium chlorides (where n is 0, $R^5$ is methyl and A is a chloride ion), and certain polyoxyethylene N-methyl alkyletherammonium chlorides (where n is 1-5, $R^5$ is methyl and A is a chloride ion). Suitable examples are polyoxyethylene (2) cocoamine, polyoxyethylene (5) tallowamine and polyoxyethylene (10) cocoamine, available for example from Akzo-Nobel as Ethomeen™ C/12, Ethomeen™ T/15 and Ethomeen™ C/20 respectively; a surfactant conforming, when its amine group is non-protonated, to formula (III):

where $R^1$ is $C_{12-14}$ alkyl, n is 3 and x+y has an average value of about 5, as disclosed in U.S. Pat. No. 5,750,468 to Wright et al., incorporated herein by reference; and polyoxyethylene (2) N-methyl cocoammonium chloride and polyoxyethylene (2) N-methyl stearylammonium chloride, available for example from Akzo-Nobel as Ethoquad™ C/12 and Ethoquad™ 18/12 respectively. In cases where $R^5$ is hydrogen, i.e., in tertiary amine as opposed to quaternary ammonium surfactants, the anion A is typically not supplied with the surfactant. However, in a glyphosate salt formulation at a pH of about 4-5, the surfactant will be protonated and it will be recognized that the anion A can be glyphosate, which is capable of forming dibasic salts. In one sub-embodiment a sole or major surfactant component is a polyoxyethylene alkylamine surfactant wherein n is 0 and x+y is 2 to about 8, as disclosed in U.S. Pat. No. 5,668,085 to Forbes et al., incorporated herein by reference. In another sub-embodiment a sole or major surfactant component is a polyoxyethylene alkylamine surfactant wherein n is 0 and x+y is about 7 to about 15, for example about 8 to about 12, optionally accompanied by a lesser amount of a polyoxyethylene alkylamine surfactant wherein n is 0 and x+y is 2 to about 5. A suitable example is polyoxyethylene (10) tallowamine, optionally blended with a lesser amount of polyoxyethylene (2) cocoamine.

In a variant of subtype B3, $R^6$ and $R^7$ are other than hydrogen. For example, the surfactant of formula (III) is a member of a class conforming to formula (IIIa):

where $R^1$, n, x and y are as defined above, and $R^6$ and $R^7$ are independently selected from hydrogen, $C_{1-4}$ alkyl, $C_{2-4}$ acyl and $C_{1-4}$ carboxylic acid groups and $C_{1-4}$ alkyl esters of $C_{1-4}$ carboxylic acid groups. Illustratively $R^6$ and $R^7$ are the same and are selected from —H, —$CH_3$, —$C_2H_5$, —$CH(CH_3)_2$, —COOH, —$COOCH_3$, —$COOC_2H_5$, —$CH_2COOH$, —$CH_2COOCH_3$ and —$CH_2COOC_2H_5$ groups.

Subtype B4: $R^5$ is an anionic oxide group and t is 0. This subtype includes commercial surfactants collectively known in the art or referred to herein as alkyldimethylamine oxides (where n, x and y are 0, and $R^6$ and $R^7$ are methyl), alkyletherdimethylamine oxides (where n is 1-5, x and y are 0, and $R^6$ and $R^7$ are methyl), polyoxyethylene alkylamine oxides (where n is 0, x+y is at least 2, and $R^6$ and $R^7$ are hydrogen), and certain polyoxyethylene alkyletheramine oxides (where n is 1-5, x+y is at least 2, and $R^6$ and $R^7$ are hydrogen). Suitable examples are cocodimethylamine oxide and polyoxyethylene (2) cocoamine oxide, available for example from Akzo-Nobel as Aromox™ DMC and Aromox™ C/12 respectively.

Subtype B5: $R^5$ is an acetate group, x and y are 0 and t is 0. This subtype includes commercial surfactants collectively known in the art or referred to herein as alkylbetaines (where n is 0 and $R^6$ and $R^7$ are methyl) and certain alkyletherbetaines (where n is 1-5 and $R^6$ and $R^7$ are methyl). A suitable example is cocobetaine, available for example from Cognis as Velvetex™ AB-45.

Type C: surfactants corresponding to formula (II) where $R^1$ is a $C_{8-18}$ aliphatic hydrocarbyl chain, m is 1, X is an ether linkage, $R^2$ is n-propylene and n is 0. In this type $R^1$ together with $OR^2$ can be considered the hydrophobic moiety of the surfactant which is attached directly by the $R^2$ linkage to the amino function. These surfactants are a subclass of alkyletheramines as disclosed in above-cited U.S. Pat. No. 5,750,468. Illustrative subtypes have the different hydrophilic moieties exemplified in subtypes B1 to B5 above. Suitable examples are a surfactant conforming, when its amine group is non-protonated, to formula (IV):

and a surfactant conforming to formula (V):

and a surfactant conforming to formula (VI):

where, in each of formulas (IV), (V) and (VI), $R^1$ is $C_{10-14}$ alkyl (e.g., isodecyl, isotridecyl or cocoalkyl) and x+y has an average value of about 5, as disclosed in above-cited U.S. Pat. No. 5,750,468.

Type D: surfactants conforming to formula (II) where $R^1$ is a $C_{8-18}$ aliphatic hydrocarbyl chain, m is 1-5, each $XR^2$ is a group —$OCH(CH_3)CH_2$— and n is 0. In this type $R^1$ together with the —$OCH(CH_3)CH_2$— group(s) can be considered the hydrophobic moiety of the surfactant which is attached directly to the amino function. These surfactants are a further subclass of alkyletheramines as disclosed in above-cited U.S. Pat. No. 5,750,468. Illustrative subtypes have the different hydrophilic moieties exemplified in subtypes B1 to B5 above. A suitable example is a surfactant conforming, when its amine group is non-protonated, to formula (VII):

where $R^1$ is $C_{12-15}$ alkyl and x+y has an average value of about 5, as disclosed in above-cited U.S. Pat. No. 5,750,468.

The surfactant of formula (VII) is a member of a class conforming to formula (VIIa):

where $R^1$, x and y are as defined above, and $R^6$ and $R^7$ are independently selected from hydrogen, $C_{1-4}$ alkyl, $C_{2-4}$ acyl and $C_{1-4}$ carboxylic acid groups and $C_{1-4}$ alkyl esters of $C_{1-4}$ carboxylic acid groups. Illustratively $R^6$ and $R^7$ are the same and are selected from —H, —$CH_3$, —$C_2H_5$, —$CH(CH_3)_2$, —COOH, —COOCH$_3$, —COOC$_2$H$_5$, —CH$_2$COOH, —CH$_2$COOCH$_3$ and —CH$_2$COOC$_2$H$_5$ groups.

Type E: surfactants corresponding to formula (II) where R$^1$ is a C$_{8-18}$ aliphatic hydrocarbyl chain, m is 1, X is an amide linkage, R$^2$ is n-propylene and n is 0. In this type R$^1$ together with XR$^2$ can be considered the hydrophobic moiety of the surfactant which is attached directly by the R$^2$ linkage to the amino function. Commonly x and y are 0, R$^5$ is hydrogen or C$_{1-4}$ alkyl, R$^6$ and R$^7$ are independently C$_{1-4}$ alkyl and t is 1. A suitable example is cocoamidopropyl dimethylamine propionate, available for example from McIntyre as Mackalene™ 117.

Type F: surfactants corresponding to formula (II) where R$^1$ is hydrogen, m is 3-8 and each XR$^2$ is a group —OCH(CH$_3$)CH$_2$—. In this type the polyether chain of —OCH(CH$_3$)CH$_2$— groups (a polyoxypropylene chain) can be considered the hydrophobic moiety of the surfactant which is linked directly or via one or more oxyethylene units to the amino function. Commonly x and y are 0, R$^5$, R$^6$ and R$^7$ are independently C$_{1-4}$ alkyl and t is 1. Such surfactants are a subclass of polyoxypropylene quaternary ammonium surfactants as disclosed in U.S. Pat. No. 5,652,197 to Claude et al., incorporated herein by reference. In a suitable example, m is 7, n is 1, R$^5$, R$^6$ and R7 are methyl and A is a chloride ion.

In surfactants of any of the above types where t is 1, A can be any suitable anion, for example chloride, bromide, iodide, sulfate, ethosulfate, phosphate, acetate, propionate, succinate, lactate, citrate, tartrate or, as indicated above, glyphosate.

In another embodiment a major or sole surfactant component comprises an N—(C$_{8-18}$) acyl sarcosinate surfactant as disclosed in above-cited WO 99/21424. Suitable examples are N-lauroyl, N-cocoyl, N-oleoyl and N-stearoyl sarcosinates.

In another embodiment at least one surfactant is present in the composition, selected from the group consisting of polyoxyethylene fatty amines having 2 to about 12 moles of ethylene oxide per mole of fatty amine, alkyletheramines, quaternary ammonium surfactants, polyoxyethylene alkylphenols, alkyl polyglycosides, alkylbetaines, alkylamine oxides and mixtures thereof.

Compositions of the invention can optionally contain additional herbicidally inactive ingredients such as pH modulating agents (e.g., acidifying, basifying and/or buffering agents), defoaming agents, antidrift agents, coloring agents, and the like. Such additional ingredients should be selected so as not to require reduction of glyphosate a.e. concentration below about 360 g/l, nor significantly compromise physical stability at high glyphosate a.e. concentration, nor antagonize herbicidal activity of the composition to an unacceptable degree.

Compositions of the invention can optionally contain one or more additional herbicides (i.e., other than glyphosate). In practice, at the high glyphosate a.e. concentrations of the present compositions, the amount of a second herbicide that can be accommodated in a stable formulation is rather limited, but in certain situations a small amount of a herbicide such as glufosinate, an imidazolinone or a sulfonylurea can be useful.

Highly concentrated aqueous potassium glyphosate compositions exhibit relatively low viscosity and high density by comparison with IPA glyphosate compositions having equal glyphosate a.e. concentration. However, potassium glyphosate is much less compatible with a wide range of surfactants than IPA glyphosate, rendering the potassium salt less useful for preparing surfactant-containing formulations with high glyphosate loading. It is surprising and unexpected, therefore, that by admixture of a relatively small amount of IPA glyphosate with potassium glyphosate in accordance with the present invention, a highly concentrated aqueous glyphosate formulation can be prepared having favorable viscosity and density properties, yet capable of containing an agronomically useful amount of any of a wide range of surfactants that are poorly compatible with potassium glyphosate alone.

An aqueous concentrate composition containing a mixture of potassium and IPA salts of glyphosate at a mole ratio of about 70:30 to about 90:10 and at a total glyphosate a.e. concentration illustratively of about 400 to about 600 g/l in accordance with the invention, with or without surfactant, can exhibit a lower freezing point than a comparative potassium salt composition. In the present context a "comparative salt composition" is one similar in all respects, including glyphosate a.e. concentration and surfactant content, to the composition of the invention, except that all glyphosate is present as the indicated salt.

Furthermore, an aqueous concentrate composition containing a mixture of potassium and IPA salts of glyphosate at a mole ratio of about 70:30 to about 90:10 and at a total glyphosate a.e. concentration illustratively of about 400 to about 600 g/l in accordance with the invention, with or without surfactant, can exhibit a lower pour point than a comparative potassium salt composition. By "pour point" is meant a temperature below which the composition is frozen or too viscous to be readily poured from a container.

Furthermore, an aqueous concentrate composition containing a mixture of potassium and IPA salts of glyphosate at a mole ratio of about 70:30 to about 90:10 and at a total glyphosate a.e. concentration illustratively of about 400 to about 600 g/l in accordance with the invention, with or without surfactant, can exhibit, at any selected temperature above the pour point, lower viscosity than a comparative IPA salt composition. This is a particularly great advantage where large volumes of the concentrate composition are to be transferred by gravity or by pumping, especially at low temperatures as can occur in early spring.

Figure 1:
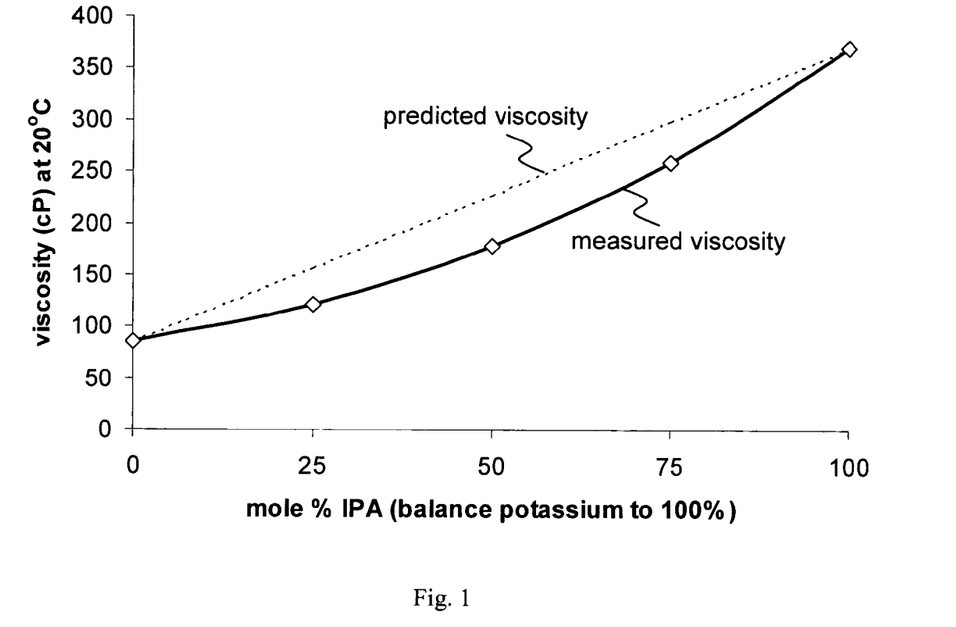
FIG. 1 is a graph showing measured viscosity at 20° C. of mixtures of glyphosate potassium and IPA salts, by comparison with predicted viscosity based on viscosities of straight potassium salt and straight IPA salt.

Surprisingly, as shown in FIG. 1, mixed concentrated solutions of glyphosate potassium and IPA salts have been found to have lower viscosity than would be predicted from the viscosities of straight potassium salt and IPA salt solutions. The data in FIG. 1 are derived from mixtures of concentrated (46.0% a.e.) glyphosate IPA salt and concentrated (47.4% a.e.) glyphosate potassium salt.

By interpolation in the graph of FIG. 1, it can be seen that a mixture comprising about 20 mole % IPA (and about 80 mole % potassium) has a viscosity that would have been predicted for a mixture comprising only about 10 mole % IPA. In other words, the effect on viscosity of adding a relatively small amount of IPA salt to potassium salt is much less than expected. A mixture of potassium and IPA salts of glyphosate at a mole ratio of about 70:30 to about 90:10 and at a total glyphosate a.e. concentration illustratively of about 400 to about 600 g/l in accordance with the invention therefore substantially enjoys the low viscosity advantages of straight potassium salt.

In various embodiments, a composition of the invention in absence of surfactant has a viscosity at 0° C. of not greater than about 300 cP, not greater than about 200 cP, not greater than about 150 cP, or not greater than about 100 cP. At glyphosate a.e. loadings lower than about 400 g/l, for example about 360 g/l, low temperature viscosity advantages of a mixed salt formulation as described herein over a straight IPA glyphosate composition are less pronounced than at higher loadings, but can still be sufficient to provide a useful benefit.

Furthermore, an aqueous concentrate composition containing a mixture of potassium and IPA salts of glyphosate at a mole ratio of about 70:30 to about 90:10 and at a total glyphosate a.e. concentration of about 400 to about 600 g/l in accordance with the invention, with or without surfactant, can exhibit higher density than a comparative IPA salt composition. Thus a given weight of glyphosate a.e. can be accommodated in a lesser volume than is required for the comparative composition. At glyphosate a.e. loadings lower than about 400 g/l, for example about 360 g/l, density advantages of a mixed salt formulation as described herein over a straight IPA glyphosate composition are less pronounced than at higher loadings, but can still be sufficient to provide a useful benefit.

Surfactant incompatibility with a concentrated glyphosate salt solution can be expressed in various ways, but generally results in a loss of physical stability, at low or more particularly at high temperatures. As glyphosate formulations are required to be stored in a wide range of temperature conditions, such loss of physical stability is highly undesirable.

A particularly useful measure of physical stability for surfactant-containing aqueous concentrate formulations of glyphosate salts is cloud point. Cloud point is a measure of the maximum temperature at which a specific such formulation forms a single-phase solution. At temperatures above the cloud point, the surfactant separates from the solution, initially as a hazy or cloudy dispersion, and, upon standing, as a distinct phase generally rising to the surface of the solution. Cloud point of a composition can be determined by heating the composition until the solution becomes cloudy, and then allowing the composition to cool, with agitation, while its temperature is continuously monitored. A temperature reading taken when the solution clears is a measure of cloud point.

What constitutes an acceptable cloud point is arbitrary, but for most purposes cloud point should be not lower than about 45° C., for example not lower than about 50° C., not lower than about 55° C., or not lower than about 60° C. Thus by one definition, a surfactant that is acceptably "compatible" in an aqueous concentrate glyphosate composition of the invention is one that, when present in a 360 g a.e./l composition at a glyphosate a.e./surfactant ratio of 10:1 by weight, exhibits a cloud point not lower than about 45° C. Other, more stringent, definitions of compatibility can be set forth by specifying a higher glyphosate a.e. concentration, for example 400 g a.e./l, a lower glyphosate a.e./surfactant ratio (i.e., a higher surfactant concentration for a given glyphosate a.e. concentration) and/or a higher cloud point.

It should be noted that where no cloud point exists or where a cloud point cannot be determined because the composition remains a single-phase solution at the highest temperature tested (typically about 95° C.), for the purposes of the above definitions the composition is deemed to have a cloud point of >95° C.

Surprisingly, a number of surfactants that are known to be incompatible with potassium glyphosate nonetheless exhibit acceptable cloud points in aqueous concentrate compositions of the present invention, in some cases when the glyphosate a.e./surfactant ratio is as low as 4:1.

Methods of use of glyphosate herbicidal formulations are well known in the art. An aqueous concentrate composition of the invention can be diluted in an appropriate volume of water to provide an application composition that can then be applied, for example by spraying, to foliage of plants such as weeds to be killed or controlled. For most purposes, an application composition, for example a spray-tank composition, is applied at a glyphosate a.e. rate of about 0.1 to about 5 kg/ha, occasionally more. Typical glyphosate a.e. rates for control of annual and perennial grasses and broadleaved plants are about 0.3 to about 1.5 kg/ha. A composition of the invention can be applied in any convenient volume of water, most typically about 50 to about 1,000 l/ha.

It is not an object of the present invention to provide enhanced herbicidal efficacy, as is said to be provided, for example, by the formulations disclosed in above-cited WO 03/013241. It is possible that a composition of the invention having a mixture of potassium and IPA salts of glyphosate could exhibit greater efficacy on particular plant species under particular conditions than a similar composition having only potassium glyphosate or only IPA glyphosate, but that is not a requirement herein. In general, a composition of the invention can be expected to exhibit bioefficacy, over a wide range of species and conditions, that is comparable to straight potassium salt or straight IPA salt formulations, at the same glyphosate a.e. rates and in presence of the same surfactants.

According to one embodiment, in the method of use described above, an application composition is prepared by tank-mixing a glyphosate composition of the invention with a coherbicide of low water solubility. Such a coherbicide can be supplied, for example, in a form of a suspension concentrate formulation. Tank-mixing is of great benefit where two or more herbicides are to be applied to the same area of land, as it permits great saving in time and fuel cost by comparison with making two passes over the same area to apply the herbicides one after the other.

Many suspension concentrate herbicide formulations exhibit poor tank-mix compatibility with surfactant-containing glyphosate formulations, in particular surfactant-containing potassium glyphosate formulations. Poor compatibility can be exhibited in various ways, including a tendency for precipitation or flocculation of the herbicide of low water solubility, leading to settling in the spray tank and, in some cases, blocking of spray nozzles.

According to an embodiment of the present invention, it has been found that polyoxyethylene tertiary amine and etheramine surfactants having an average of at least about 7, for example about 7 to about 15, or about 8 to about 12, EO units (herein "high-EO surfactants") provide enhanced tank-mix compatibility of glyphosate salts with suspension concentrate formulations of insoluble coherbicides such as atrazine (e.g., Aatrex® 4L herbicide of Syngenta), prometryn (e.g., Caparol® 4L herbicide of Syngenta), fluometuron (e.g., Cotoran® herbicide of Makhteshim-Agan) and diuron (e.g., Direx® 4L of Griffin Corporation), by comparison with similar surfactants having fewer EO units. It has further been found that mixed potassium/propylammonium glyphosate compositions as described herein, unlike straight potassium glyphosate compositions at the same a.e. concentration, can be formulated with certain high-EO surfactants at a weight ratio of glyphosate a.e. to surfactant of 10:1 or lower. Thus the present invention unexpectedly provides, according to the present embodiment, a highly concentrated glyphosate formulation that exhibits good tank-mix compatibility with suspension concentrate formulations of water-insoluble coherbicides.

Optionally a composition of the present embodiment can further comprise a polyoxyethylene tertiary amine or etheramine surfactant having an average of no more than about 5 EO units (herein "low-EO surfactant"). In the case of a glyphosate composition of the invention comprising a blend of high-EO and low-EO surfactants, acceptable tank-mix compatibility will generally be found at a weight ratio of high-EO to low-EO surfactants of at least about 40:60, for example at least about 50:50, at least about 70:30, or at least about 80:20, illustratively about 85:15 to about 95:5.

An illustrative surfactant useful in a composition of the invention is a polyoxyethylene fatty amine having about 7 to about 15 EO units, optionally in a blend with a polyoxyethylene fatty amine having about 2 to about 5 EO units. Such fatty amines can, without limitation, independently be selected from tallowamines, hydrogenated tallowamines, stearylamines, oleylamines, cetylamines, myristylamines, soyamines, cocoamines, laurylamines and mixtures thereof. For example, a high-EO tallowamine such as one having about 7.5, about 8, about 8.5, about 9, about 9.5, about 10, about 10.5, about 11, about 11.5, about 12, about 12.5, about 13, about 13.5, about 14, about 14.5 or about 15 EO units can optionally be blended with a low-EO cocoamine such as one having about 2, about 2.5, about 3, about 3.5, about 4, about 4.5 or about 5 EO units. Either or both of the tallowamine and the cocoamine components of such a blend can optionally be substituted, in whole or in part, with another fatty amine, for example a soyamine component. A suitable weight ratio of high-EO to low-EO fatty amine in such a blend can be, for example, about 50:50, about 55:45, about 60:40, about 65:35, about 70:30, about 75:25, about 80:20, about 85:15 or about 90:10.

Another illustrative surfactant useful in a composition of the invention is an etheramine surfactant similar to that of formula (VII) but wherein x+y has an average value of about 7 to about 15, for example about 7.5, about 8, about 8.5, about 9, about 9.5 or about 10. An example of such a surfactant wherein x+y has an average value of about 8 is referred to herein as "etheramine 8EO". Such an etheramine can optionally be blended with a low-EO surfactant, for example a low-EO fatty amine surfactant such as a cocoamine having about 2, about 2.5, about 3, about 3.5, about 4, about 4.5 or about 5 EO units, at a weight ratio of about 40:60 to about 95:5, for example about 50:50, about 55:45, about 60:40, about 65:35, about 70:30, about 75:25, about 80:20, about 85:15 or about 90:10.

In a further embodiment, a tank-mix herbicidal composition is provided. This ready-to-use application composition comprises, in an aqueous application medium, a glyphosate herbicide and a coherbicide of low water solubility, the composition being prepared by a process comprising admixing in a suitable vessel with agitation:

(i) water in an amount suitable for application to a plant and/or soil surface by spraying;

(ii) a herbicidally effective amount of an aqueous concentrate herbicidal composition comprising in aqueous solution a mixture of salts of glyphosate at a total glyphosate a.e. concentration not less than about 360 g/l, wherein (a) said glyphosate is in anionic form accompanied by low molecular weight non-amphiphilic cations in a total molar amount of about 100% to about 120% of the molar amount of said glyphosate; (b) said cations comprise potassium and propylammonium (e.g., IPA) cations in a mole ratio of about 50:50 to about 90:10; and (c) said potassium and propylammonium cations together constitute about 90 to 100 molar percent of all of said low molecular weight non-amphiphilic cations in the composition; said composition further comprising as a major or sole surfactant component a polyoxyethylene tertiary amine or etheramine surfactant comprising on average at least about 7 EO units; and (iii) a herbicidally effective amount of a suspension concentrate formulation comprising the coherbicide.

The mole ratio of potassium to propylammonium cations can illustratively be about 60:40 to about 90:10, for example about 70:30 to about 90:10, about 75:25 to about 85:15, or about 77:23 to about 83:17, illustratively about 80:20. Illustratively, the total glyphosate a.e. concentration in the aqueous concentrate herbicidal composition is not less than about 400 g/l.

The composition optionally further comprises as a second surfactant component a polyoxyethylene tertiary amine or etheramine surfactant comprising on average no more than about 5 EO units. If such a second surfactant component is present, the weight ratio of first to second surfactant components can illustratively be at least about 40:60, for example at least about 70:30, or at least about 80:20, for example about 85:15 to about 95:5.

The weight ratio of glyphosate a.e. to total surfactant is typically not greater than about 10:1, for example about 2:1 to about 10:1. Illustratively the weight ratio of glyphosate a.e. to total surfactant is about 2.5:1 to about 8:1, for example about 3:1 to about 6:1.

The coherbicide of low water solubility is illustratively selected from the group consisting of atrazine, diuron, flumeturon and prometryn.

In a further embodiment of the invention, a batchwise process is provided for preparing a glyphosate salt solution that comprises potassium and IPA cations in a mole ratio of about 50:50 to about 90:10 and has a glyphosate a.e. concentration not less than about 360 g/l, for example not less than about 400 g/l. The invention is not, however, limited by processes described herein.

A batchwise process of the present embodiment comprises at least two steps. In a first step, glyphosate acid is added to a glyphosate potassium salt solution having a glyphosate assay of at least about 40% a.e. by weight, to form a slurry. In a second step, isopropylamine, in an amount sufficient to neutralize the added glyphosate acid, is introduced to the slurry with mixing until all glyphosate is dissolved, to form a mixed glyphosate salt solution comprising potassium and IPA cations in the desired mole ratio. Neutralization of glyphosate acid is exothermic and it will generally be desirable to make provision for heat removal during the second step of this batchwise process.

The glyphosate acid can be added in substantially dry form or, conveniently, in a form of "wet cake", which can typically contain up to about 15% by weight of water.

If desired, n-propylamine can be substituted for isopropylamine. Especially where very high glyphosate a.e. concentration (for example greater than about 540 g/l) is desired in the final product, it is desirable to use isopropylamine in anhydrous form, to avoid introducing more water than necessary.

Relative amounts of potassium salt, glyphosate acid and isopropylamine are selected to provide a mixed glyphosate salt solution having a desired mole ratio of potassium to IPA cations of about 50:50 to about 90:10, for example about 60:40 to about 90:10, about 70:30 to about 90:10, about 75:25 to about 85:15, or about 77:23 to about 83:17, illustratively about 80:20.

In an optional third step of the process, water is added to the mixed glyphosate salt solution to adjust glyphosate a.e. concentration of the mixed salt solution to a desired level not less than about 360 g/l, for example not less than about 400 g/l.

In a still further embodiment of the invention, a continuous process is provided for preparing a finished composition in a form of a glyphosate salt solution that comprises potassium and IPA cations in a mole ratio of about 50:50 to about 90:10 and has a glyphosate a.e. concentration not less than about 360 g/l, for example not less than about 400 g/l. This process is shown diagrammatically in FIG. 2.

Figure 2:
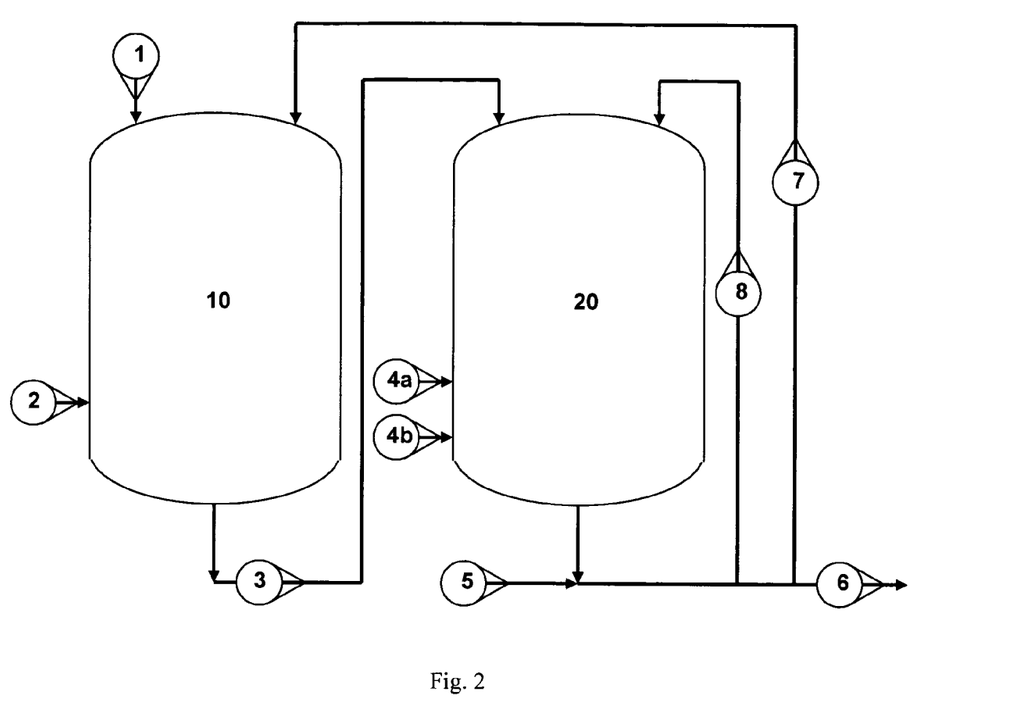
FIG. 2 is a diagram of a continuous process illustrative of an embodiment of the present invention.

A first tank 10 continuously receives recycled finished composition as stream 7. Glyphosate acid is continuously introduced as stream 1 and optionally water as stream 2 to first tank 10, the contents of which are agitated to promote mixing to form a slurry. The slurry is continuously pumped forward as stream 3 to a second tank 20 where agitation continues. A concentrated (e.g., about 45% to about 50% by weight) KOH solution is continuously added as stream 4a and isopropylamine (e.g., anhydrous) is continuously added as stream 4b to the slurry in second tank 20. The KOH and isopropylamine are added in the desired mole ratio and in a total amount sufficient to react with and neutralize the glyphosate acid added in the first step. Streams 4a and 4b can optionally be merged before feeding to second tank 20, but are preferably kept apart prior to entry to the tank and are preferably added subsurface to the slurry. The contents of second tank 20 are continuously recirculated as stream 8, optionally through a heat exchanger to remove excess heat of reaction. Parameters of the resulting solution such as density, temperature and pH can be measured in stream 8 and the resulting data used in process control. Water is added as stream 5 if necessary to adjust the solution to the desired glyphosate a.e. concentration. The resulting finished composition is drawn from second tank 20 and divided into stream 7, which is continuously recycled to first tank 10, and stream 6, which is continuously removed as finished product and transferred, for example, to a storage tank (not shown).

As in the batchwise process, the glyphosate acid can be added in substantially dry form or as wet cake. If desired, n-propylamine can be substituted for isopropylamine. Relative amounts of glyphosate acid, KOH and isopropylamine are selected to provide a mixed glyphosate salt solution having a desired mole ratio of potassium to IPA cations of about 50:50 to about 90:10, for example about 60:40 to about 90:10, about 70:30 to about 90:10, about 75:25 to about 85:15, or about 77:23 to about 83:17, illustratively about 80:20.

The invention is further illustrated but not limited by the following Examples.

EXAMPLES

Example 1

Aqueous solutions of glyphosate salts were prepared, each at a glyphosate a.e. concentration of 540 g/l, using straight potassium salt, straight IPA salt or a mixture of potassium and IPA salts at a mole ratio of 80:20. For each composition, the following data were obtained: density at 25° C.; viscosity at each of 20° C., 10° C. and 0° C.; and approximate freezing point. Approximate freezing point was determined by holding the composition at progressively (5 degree intervals) lower temperatures, each for a 24-hour equilibration period, and observing the percentage of the volume of the composition that was frozen. Data are presented in Table 1.

TABLE 1

Properties of 540 g a.e./l glyphosate salt solutions

| | density | viscosity (cP) | | | freezing |
|---|---|---|---|---|---|
| | 25° C. | 20° C. | 10° C. | 0° C. | point |
| 100% potassium | 1.3576 | 16 | 25 | 41 | −20° C. |
| 80% potassium, 20% IPA | 1.3316 | 26 | 42 | 76 | <−30° C. |
| 100% IPA | 1.2377 | 175 | 372 | 946 | <−30° C. |

Example 2

Aqueous concentrate formulations of mixed potassium and IPA salts of glyphosate were prepared, each containing the etheramine surfactant of formula (VII) above at a glyphosate a.e. to surfactant ratio of 4:1 by weight. Formulations were prepared at three different glyphosate a.e. concentrations, using each of two different mole ratios of potassium to IPA salt. For each composition, the following data were obtained: density at 25° C.; and viscosity at each of 20° C., 10° C. and 0° C. Data are presented in Table 2.

TABLE 2

Properties of mixed glyphosate salt solutions containing etheramine surfactant

| concentration (g/l) | | mole % | | density | viscosity (cP) | | |
|---|---|---|---|---|---|---|---|
| glyphosate a.e. | surfactant | K salt | IPA salt | 25° C. | 20° C. | 10° C. | 0° C. |
| 480 | 120 | 67 | 33 | 1.2823 | 65 | 114 | 288 |
| 540 | 135 | 67 | 33 | 1.3126 | 183 | 367 | 859 |
| 600* | 150 | 67 | 33 | 1.3188 | 236 | 488 | 1190 |
| 480 | 120 | 80 | 20 | 1.2961 | 51 | 82 | 151 |
| 540 | 135 | 80 | 20 | 1.3301 | 125 | 233 | 505 |
| 600* | 150 | 80 | 20 | 1.3440 | 199 | 393 | 919 |

*target concentration; actually 590 g/l due to raw material concentration limits

Example 3

Aqueous concentrate formulations of glyphosate salts were prepared, each at a glyphosate concentration of 540 g/l, using straight potassium salt, straight IPA salt or a mixture of potassium and IPA salts at a mole ratio of 80:20, and each containing the etheramine surfactant of formula (VII) above at a glyphosate a.e. to surfactant ratio of 4:1 by weight. For each composition, the following data were obtained: density at 25° C.; and viscosity at each of 20° C., 10° C. and 0° C. Data are presented in Table 3.

TABLE 3

Properties of glyphosate salt solutions containing etheramine surfactant

| concentration (g/l) | | mole % | | density | viscosity (cP) | | |
|---|---|---|---|---|---|---|---|
| glyphosate a.e. | surfactant | K salt | IPA salt | 25° C. | 20° C. | 10° C. | 0° C. |
| 540 | 135 | 100 | 0 | 1.3594 | 84 | 133 | 259 |
| 540 | 135 | 80 | 20 | 1.3336 | 136 | 257 | 569 |
| 540 | 135 | 0 | 100 | 1.2124 | 481 | 1121 | 3120 |

Example 4

The compositions of Example 3 were tested for herbicidal effectiveness in a greenhouse study on 3-4 weeks old velvetleaf (*Abutilon theophrasti*, ABUTH) and prickly sida (*Sida spinosa*, SIDSP) plants. Each composition was diluted in water and applied by a laboratory track sprayer calibrated to deliver a spray volume of 93 l/ha at a pressure of 165 kPa through a 9501E flat fan nozzle. Four rates of application were tested for each composition. Herbicidal effectiveness was recorded as percent control, 19 days after application. Results are presented in Table 4.

TABLE 4

Herbicidal effectiveness (% control) of compositions of Example 3

| composition | | | | % control | | | | | | | |
|---|---|---|---|---|---|---|---|---|---|---|---|
| concentration (g/l) | | mole % | | ABUTH, g a.e./ha: | | | | SIDSP, g a.e./ha: | | | |
| glyphosate a.e. | surfactant | K salt | IPA salt | 100 | 200 | 300 | 400 | 100 | 200 | 300 | 400 |
| 540 | 135 | 100 | 0 | 10 | 53 | 84 | 84 | 11 | 57 | 68 | 83 |
| 540 | 135 | 80 | 20 | 30 | 32 | 79 | 79 | 31 | 72 | 73 | 80 |
| 540 | 135 | 0 | 100 | 10 | 43 | 80 | 81 | 20 | 58 | 69 | 80 |

Example 5

A mixture of potassium and IPA salts of glyphosate at a mole ratio of 80:20 was formulated at a glyphosate a.e. concentration of 540 g/l, together with different polyoxyethylene tallowamine surfactants differing in average number of EO units, in each case at a glyphosate a.e. to surfactant ratio of 4:1 by weight. Cloud point of each formulation was determined by the following procedure. A sample of the formulation in a test tube was heated in a water bath until it became cloudy. The test tube was then removed from the water bath to allow to cool gradually towards room temperature, and the sample was stirred until it became clear. Temperature of the sample was recorded when the sample became clear; this temperature was recorded as cloud point. Data are presented in Table 5.

TABLE 5

Cloud point of mixed glyphosate salt (80% potassium, 20% IPA) formulations

| concentration (g/l) | | surfactant | cloud |
|---|---|---|---|
| glyphosate a.e. | surfactant | type | point |
| 540 | 135 | tallowamine 10.5EO | <room temp. |
| 540 | 135 | tallowamine 8EO | 53° C. |
| 540 | 135 | tallowamine 6EO | 82° C. |

Example 6

A mixture of potassium and IPA salts of glyphosate at a mole ratio of 80:20 was formulated at a glyphosate a.e. concentration of 540 g/l, together with the etheramine surfactant of formula (VII) above at a glyphosate a.e. to surfactant ratio of 5.34:1 by weight. A comparative formulation was prepared using straight potassium salt in place of the mixed salts.

Both formulations were placed in a freezer at −30° C. After 24 hours in the freezer, the straight potassium salt formulation was found to have a thick layer of ice on top, but no ice had formed in the formulation containing mixed potassium and IPA salts.

The samples were moved to a −20° C. freezer. After 24 hours, both formulations were found to be liquid.

The samples were moved to a −25° C. freezer. After 3 days at −25° C., the straight potassium salt formulation was found to have an ice layer, but the mixed salt formulation remained liquid.

Example 7

A mixture of potassium and IPA salts of glyphosate at a mole ratio of 80:20 was formulated at a glyphosate a.e. concentration of 480 g/l, together with the surfactant of formula (III) above at a glyphosate a.e. to surfactant ratio of 4:1 by weight. A comparative formulation was prepared using straight potassium salt in place of the mixed salts. Cloud point of each formulation was determined as in Example 5. Data are presented in Table 6.

TABLE 6

Cloud point of mixed glyphosate salt (80% potassium, 20% IPA) formulation by comparison with straight potassium salt formulation

| | concentration (g/l) | | surfactant | cloud |
|---|---|---|---|---|
| | glyphosate a.e. | surfactant | type | point |
| 100% potassium | 480 | 120 | etheramine, formula (III) | 63° C. |
| 80% potassium, 20% IPA | 480 | 120 | etheramine, formula (III) | >75° C. |

Both formulations were placed in a freezer at −30° C. After 24 hours in the freezer, both formulations were found to be frozen solid.

The samples were moved to a −20° C. freezer. After 48 hours, both formulations were found to be liquid.

The samples were moved to a −25° C. freezer. After 3 days at −25° C., the straight potassium salt formulation was found to be frozen solid, but the mixed salt formulation remained liquid.

Example 8

A mixture of potassium and IPA salts of glyphosate at a mole ratio of 80:20 was formulated at a glyphosate a.e. concentration of 600 g/l, together with different surfactants, in each case at a glyphosate a.e. to total surfactant ratio of 4:1 by weight. Cloud point of each formulation was determined as in Example 5. Data are presented in Table 7.

TABLE 7

Cloud point of mixed glyphosate salt (80% potassium, 20% IPA) formulations

| concentration (g/l) | | surfactant | cloud |
|---|---|---|---|
| glyphosate a.e. | surfactant | type | point |
| 600 | 150 | tallowamine 6EO | 61° C. |
| 600 | 150 | tallowamine 10.5EO + cocoamine 2EO, 55:45 by weight | 70° C. |

Example 9

Mixtures of potassium and IPA salts of glyphosate at various mole ratios were formulated at a glyphosate a.e. concentration of 540 g/l, together with a tallowamine 10.5EO+cocoamine 2EO, 90:10 by weight surfactant blend. The surfactant blend was included in the formulation at a glyphosate a.e. to total surfactant ratio of 4:1 by weight. Also included was a defoaming agent (Agnique™ DF 6889) at 0.5 g/l. Cloud point of each formulation was determined as in Example 5. Data are presented in Table 8.

TABLE 8

Cloud point of mixed glyphosate salt solutions

| concentration (g/l) | | mole % | | density | cloud |
|---|---|---|---|---|---|
| glyphosate a.e. | surfactant | K salt | IPA salt | 25° C. | point |
| 540 | 135 | 80 | 20 | unstable | |
| 540 | 135 | 75 | 25 | 1.3250 | 40° C. |
| 540 | 135 | 70 | 30 | 1.3183 | 50° C. |
| 540 | 135 | 65 | 35 | 1.3161 | 57° C. |
| 540 | 135 | 60 | 40 | 1.3094 | 62° C. |

What is claimed is:

1. A herbicidal composition comprising in aqueous solution a mixture of salts of glyphosate at a total glyphosate acid equivalent concentration of about 360 g/l or greater than 360 g/l, wherein (a) said glyphosate is in anionic form accompanied by low molecular weight non-amphiphilic cations in a total molar amount of about 100% to about 120% of the molar amount of said glyphosate; (b) said cations comprise potassium and propylammonium cations in a mole ratio of 70:30 to 90:10; and (c) said potassium and propylammonium cations together constitute about 90 to 100 molar percent of all of said low molecular weight non-amphiphilic cations in the composition.

2. The composition of claim 1 wherein the propylammonium cations consist of n-propylammonium cations, isopropylammonium cations or a mixture thereof.

3. The composition of claim 1 wherein the propylammonium cations are isopropylammonium cations.

4. The composition of claim 3 having a total glyphosate acid equivalent concentration of about 400 g/l to about 650 g/l.

5. The composition of claim 3 having a total glyphosate acid equivalent concentration of about 450 g/l to about 600 g/l.

6. The composition of claim 3 having a total glyphosate acid equivalent concentration of about 500 g/l to about 600 g/l.

7. The composition of claim 3 wherein the mole ratio of potassium to propylammonium cations is about 75:25 to about 85:15.

8. The composition of claim 1, further comprising at least one surfactant, wherein the weight ratio of glyphosate acid equivalent to total surfactant is about 10:1 or less than 10:1.

9. The composition of claim 8, wherein the weight ratio of glyphosate acid equivalent to total surfactant is about 6:1 or less than 6:1.

10. The composition of claim 8 wherein the at least one surfactant is selected from the group consisting of polyoxyethylene fatty amines having 2 to about 12 moles of ethylene oxide per mole of fatty amine, alkyletheramines, quaternary ammonium surfactants, polyoxyethylene alkylphenols, alkyl polyglycosides, alkylbetaines, alkylamine oxides and mixtures thereof.

11. The composition of claim 8 having a cloud point of about 45° C. or higher than 45° C.

12. The composition of claim 8 having a cloud point of about 60° C. or higher than 60° C.

13. The composition of claim 8 exhibiting acceptable tank-mix compatibility with at least one coherbicide formulated as a suspension concentrate and selected from the group consisting of atrazine, diuron, fluometuron and prometryn.

14. The composition of claim 1 exhibiting substantially no ice formation when stored for 24 hours at a temperature of −25° C. or higher.

15. The composition of claim 1 having in absence of surfactant a viscosity at 0° C. of about 300 cP or lower than 300 cP.

16. The composition of claim 1 having in absence of surfactant a viscosity at 0° C. of about 100 cP or lower than 100 cP.

17. A tank-mix herbicidal composition comprising, in an aqueous application medium, a glyphosate herbicide and a coherbicide of low water solubility, the composition being prepared by a process comprising admixing in a suitable vessel with agitation:
   (i) water in an amount suitable for application to a plant and/or soil surface by spraying;
   (ii) a herbicidally effective amount of an aqueous concentrate herbicidal composition comprising in aqueous solution a mixture of salts of glyphosate at a total glyphosate a.e. concentration of about 360 g/l or greater than 360 g/l, wherein (a) said glyphosate is in anionic form accompanied by low molecular weight non-amphiphilic cations in a total molar amount of about 100% to about 120% of the molar amount of said glyphosate; (b) said cations comprise potassium and propylammonium cations in a mole ratio of 70:30 to 90:10; and (c) said potassium and propylammonium cations together constitute about 90 to 100 molar percent of all of said low molecular weight non-amphiphilic cations in the composition; said composition further comprising as a major or sole surfactant component a polyoxyethylene tertiary amine or etheramine surfactant comprising on average about 7 or more than 7 EO units; and
   (iii) a herbicidally effective amount of a suspension concentrate formulation comprising the coherbicide.

18. The composition of claim 17 wherein the mole ratio of potassium to propylammonium cations is about 2.5:1 to about 7.5:1.

19. The composition of claim 1 wherein the mole ratio of potassium to propylammonium cations is about 2.5:1 to about 7.5:1.

* * * * *